(12) United States Patent
Cruz et al.

(10) Patent No.: US 7,494,684 B2
(45) Date of Patent: Feb. 24, 2009

(54) METHOD FOR THE PREPARATION OF A STABLE ALKALI METAL LACTATE IN POWDER FORM

(75) Inventors: Eloy E Urbano Cruz, Dordrecht (NL); Peter Paul Jansen, Oss (NL); Bert Theo De Vegt, Rotterdam (NL)

(73) Assignee: Purac Biochem B.V., Gorinchem (NL)

( * ) Notice: Subject to any disclaimer, the term of this patent is extended or adjusted under 35 U.S.C. 154(b) by 5 days.

(21) Appl. No.: 10/265,633

(22) Filed: Oct. 8, 2002

(65) Prior Publication Data

US 2003/0068424 A1    Apr. 10, 2003

(30) Foreign Application Priority Data

Oct. 8, 2001    (NL) .................................. 1019140

(51) Int. Cl.
*A23L 1/22* (2006.01)
(52) U.S. Cl. ...................................... 426/652; 426/654
(58) Field of Classification Search ................. 426/650, 426/652, 654
See application file for complete search history.

(56) References Cited

U.S. PATENT DOCUMENTS 2,013,104 A * 9/1935 Macallum ..................... 203/41
4,511,584 A * 4/1985 Percel et al. .................. 426/99

FOREIGN PATENT DOCUMENTS

| GB | 395990 | | 7/1933 | |
|---|---|---|---|---|
| JP | 63225332 | * | 9/1988 | ................ 562/589 |
| JP | 63225332 A | * | 9/1988 | |
| JP | 8020556 | | 1/1996 | |
| NL | 7106959 | | 11/1972 | |

* cited by examiner

*Primary Examiner*—Arthur L Corbin
(74) *Attorney, Agent, or Firm*—Gilberto M. Villacorta; Sunit Talapatra; Foley & Lardner LLP

(57) ABSTRACT

The invention relates to a method for the preparation of a stable alkali metal lactate in powder form, the product of said preparation, functional pre-mixes for foodstuff comprising said stable alkali metal lactate powder, and foodstuffs comprising said stable alkali metal lactate powder. In the method according to the invention, a concentrate that contains alkali metal lactate is processed, with cooling, in a mixer/extruder to form a powder of the alkali metal lactate. According to the invention the alkali metal lactates in powder form are stable for at least 48 hours.

12 Claims, No Drawings

METHOD FOR THE PREPARATION OF A STABLE ALKALI METAL LACTATE IN POWDER FORM

1.0 FIELD OF THE INVENTION

The invention relates to the preparation of a stable alkali metal lactate in powder form, in particular, a stable sodium lactate in powder form, the product of said preparation, functional pre-mixes for foodstuff comprising said stable alkali metal lactate powder, and foodstuffs comprising said stable alkali metal lactate powder.

2.0 BACKGROUND OF THE INVENTION

Sodium lactate is, inter alia, an important constituent in various flavouring mixtures. For the preparation of a flavouring mixture in powder form, it is important to be able to use sodium lactate in powder form. The stability of, in particular, open packs is an important criterion here. For good processing of sodium lactate in powder form in such flavouring mixtures, the stability of the sodium lactate in powder form is preferably at least 48 hours.

Sodium lactate in powder form is currently produced by crystallisation of a concentrated sodium lactate solution in absolute ethanol. Because of its highly hygroscopic properties, this powder has limited stability; it absorbs moisture very rapidly and in doing so forms a viscous fluid (as a rule within one hour and often after only 15 minutes).

Netherlands Patent Application 7106959 discloses a method for the preparation of sodium lactate in powder form with which an aqueous sodium lactate solution is spray-dried in a spray tower. With this method a glassy product may be formed on the wall of the spray tower.

This can largely be prevented by spray-drying a cooking salt solution first and then spray-drying the sodium lactate solution. This product, however, lacks the desired stability. The starting point for the present invention is a different method for removing water wherein sodium lactate is made in powder form in a less-energy costly way. The powder obtained with said method appears to have the desired stability.

3.0 SUMMARY OF THE INVENTION

The invention provides a solution to the stability problem described above and relates to a method for the preparation of a stable alkali metal lactate in powder form, wherein a concentrate that contains alkali metal lactate is processed, with cooling, in a mixer/extruder to form a powder of the alkali metal lactate.

4.0 DESCRIPTION OF THE SPECIFIC EMBODIMENTS

According to the invention, the alkali metal lactate is preferably lithium lactate, sodium lactate or potassium lactate and, in particular, sodium lactate. According to the invention the alkali metal lactates in powder form are stable for at least 48 hours.

The starting material used for the preparation of the concentrate is an aqueous solution of the alkali metal lactate. This 50-70% (m/m), preferably 55-65% (m/m), aqueous solution is preferably first treated with active charcoal before the solution is concentrated to 60-100% (m/m), preferably 80-100% (m/m), most preferably 90-100% (m/m).

According to the invention, the processing in an extruder/mixer is preferably carried out at a starting temperature of 110° C. to 170° C., preferably 130° C. to 165° C. The cooling ranges from 10° C. to 100° C., preferably 20° C. to 90° C. Suitable extrude/mixers are Haake Rheomix 600 Models®, Hobart mixers, Werner & Pfliederer Models®, APV-Baker mixer/extruders, Simon Freres MXT models or any other comparable extruder/mixers known in the art.

If it is desirable or necessary to shorten the length of the mixer/extruder, the concentrate can first be cooled in a heat extractor column as a pretreatment. In this case, the concentrate is cooled, under the influence of gravity, in countercurrent with air/nitrogen in the boat extractor column, the concentrate being cooled by 20°-50° C. with respect to the starting temperature.

In order to improve the stability of the alkali metal lactate powder even more, the alkali metal lactate may be combined with a carrier. Said combining with a carrier may be conducted prior to being processed with cooling in the mixer/extruder to directly form a powder comprising the alkali metal lactate. With this method the concentrate used, as a starting material, may be relatively low concentrated: down to 60% (m/m). The alkali metal lactate may also be combined with a carrier after processing the concentrate with an extruder/mixer, with cooling.

The carrier that is used herein is preferably a flour, a starch, a silicate or an alkaline earth metal lactate. The flour is preferably rice flour. The starch is preferably cornstarch, wheat starch or pea starch. The silicates are preferably food-grade silicas such as Sipernat® 22S and 50S, ex Degussa and Zeothix 265. The alkaline earth metal lactate is preferably calcium lactate. With this method the ratio of alkali metal lactate carrier varies from 50:50 to 10:90, and preferably 50:50 to 40:60, based on the weight of the alkali metal lactate comprising powder.

As mentioned above, the carrier can also be combined with the alkali metal lactate after extrusion. Thus, this embodiment encompasses a method for the preparation of a stable alkali metal lactate in powder form, comprising the steps of:

(a) processing a concentrate that contains an alkali metal lactate, with cooling, in a mixer/extruder to give a powder of the alkali metal lactate; and (b) mixing the powder from step (a) with a carrier to form a powder containing alkali metal lactate.

It was found that with this method a higher concentration of alkali metal lactate in the powder may be obtained compared with the powder obtained with combined extrusion. With this method the ratio of alkali metal lactate powder:carrier is at least 99:1 to 50:50 and preferably 80:20 based on the weight of the alkali metal lactate comprising powder.

The alkali metal lactate powder is preferably ground, preferably in a conical flourmill or a hammer mill, to the desired particle size before step (b). This particle size is preferably less than 800 μm and in particular is 200 to 800 μm.

Step (b) of the method according to the above-described embodiment is preferably carried out in a mixer, for example, a Hobart mixer, a Turbula Nauta or Forberg mixer, at ambient temperature.

The stability of the stable alkali metal lactate in powder form can be even further increased by adding a suitable emulsifier, for example, sodium stearyl lactate or lecithin, either during the processing in the extruder/mixture or in step (b) when conducted. The stability and the product characteristics of the stable alkali metal lactate in powder form can be adjusted with the aid of these additives, the requisite stability duration of at least 48 hours always being met.

The alkali metal lactate powder obtained with the methods according to the invention have a stability of at least 48 hours which renders it novel and are therefore, also subject of this invention. Owing to its stability the alkali metal lactate powder according to the invention appears highly suitable for use in foodstuffs and even for functional pre-mixes for foodstuffs. Additional ingredients for functional pre-mixes comprise spices, preservatives, colourings and flavourings, etc. Said pre-mixes may be prepared by either combining the stable alkali metal lactate containing powder with the other ingredients or the other ingredients may be added to the alkali metal lactate at any stage during preparation of the stable alkali metal lactate containing powder. Irrespective of the preparation method used, the alkali metal lactate powder according to the invention, before being used in various applications, is preferably ground to a particle size of less than 800 μm, more preferably to a particle size between 200-800 μm. The invention is also directed to foodstuffs and functional premixes comprising the stable alkali metal lactate powder according to the invention.

The invention is further elucidated by the examples, which are to be construed as illustrative only and not as being limitative.

5.0 EXAMPLES

Example 1

An aqueous solution of sodium lactate that contained 60-65% (m/m) sodium lactate was evaporated, either under atmospheric pressure or under reduced pressure, to give a concentrate that contained 90% (m/m) sodium lactate. In additional experiments the aqueous solutions that contained 60-65% (m/m) sodium lactate were combined with a carrier. The carriers used were potato starch, wheat starch, corn starch, tapioca and additives such as Capsul E, sunflower oil, Esterlac EFF, salt, lecithin, glycerol, Tween 80, Span 80, and glycerol. The concentrate and the carrier were processed in a Haake Rheomix 600 model mixer/extruder to give a powder comprising about 42% (m/m) sodium lactate. The mixing times and processing temperatures were, respectively, 5 to 30 minutes and 90° C. to 130° C. The powder consisted of individual rubbery grains. These grains were stable for at least 48 hours (of the order of 2 to 5 days).

The stability of the powder was tested as follows: 5-gram sample and a 100-grain sample, respectively, of each powder were placed in an aluminum cup and in a plastic bag (26×34 cm). The stability tests were carried out in a climate-controlled chamber at 30, 60 and 70% relative humidity and at a temperature of 20° C. The values for the water absorption by the powder samples (that is to say the stability) were determined when the powder samples had visibly clearly absorbed water.

Example 2

An aqueous solution of sodium lactate that contained 60-65% (m/m) sodium lactate was evaporated, either under atmospheric pressure or under reduced pressure, to give a concentrate that contained 93-100% (m/m) sodium lactate. The concentrate was fed at a temperature of 150°-160° C. to an APV-Baker mixer/extruder. In order to reduce the length of the extruder, in a number of experiments a heat extractor column was used as pretreatment for the stream that was fed to the mixer/extruder. In the heat extractor column the concentrate introduced was cooled under the influence of gravity in counter-current with air/nitrogen; during this operation the concentrate was cooled by 20°-50° C. Irrespective of whether or not a heat extractor column was used, the product was cooled in a mixer/extruder to a final temperature of 20°-60° C.; the residence time in the mixer/extruder was 2 to 9 minutes. The product was then ground in a conical flourmill, the particle size of the ground product being less than 600 μm. The ground product was mixed with a carrier in a Hobart mixer for 10 to 120 minutes in an air or a nitrogen atmosphere. The carriers used were rice flour, cornstarch, pea starch, wheat starch, the silicate Sipernat 22S or the silicate Zeothix 265. The sodium lactate:carrier ratio was 60:40, based on the pulverulent sodium lactate.

For the stability tests a 5-gram sample and a 100-gram sample, respectively, of each powder was placed in a plastic dish (4×3 cm) and in a plastic bag (26×34 cm), respectively. The stability tests were carried out in a climate-controlled chamber at a relative humidity of 60% and a temperature of 20° C. For the 100 g sample the values for the moisture absorption by the samples were determined when the sample had visibly clearly absorbed water. The end products were found to be stable to moisture absorption for a period of 48 to 72 hours.

What is claimed is:

1. A Method for the preparation of a stable alkali metal lactate in powder form, comprising processing an aqueous concentrate of 60-100% (m/m) alkali metal lactate in a mixer/extruder at a starting temperature of 110° C. to 170° C., and cooling the alkali metal lactate concentrate to form a powder of the alkali metal lactate, wherein the alkali metal lactate concentrate is combined with a carrier before or after processing.

2. The method according to claim 1, wherein cooling is carried out down to 10° to 100° C.

3. The method according to claim 1, wherein the aqueous alkali metal lactate is treated with active charcoal before it is concentrated.

4. The method according to claim 1, wherein, during processing with cooling in a mixer/extruder the concentrate is cooled in a heat extractor column and then in a mixer/extruder.

5. The method according to claim 1, wherein the carrier is a flour, a starch, a silicate or an alkaline earth metal lactate.

6. The method according to claim 1, wherein the concentrate is combined with a carrier prior to being processed with cooling in a mixer/extruder to form a powder comprising the alkali metal lactate.

7. The method according to claim 6, wherein the alkali metal lactate:carrier ratio ranges from 50:50 to 10:90, based on the weight of the alkali metal lactate comprising powder.

8. The method according to claim 1, wherein (a) the concentrate of an alkali metal lactate is processed, with cooling, in a mixer/extruder to give a powder of the alkali metal lactate, after which (b) the powder from step (a) is mixed with a carrier to form a powder comprising the alkali metal lactate.

9. The method according to claim 8 wherein the powder of the alkali metal lactate is ground to a smaller particle size prior to step (b).

10. The method according to claim 8, wherein the alkali metal lactate powder:carrier ratio ranges from 99:1 to 50:50, based on the weight of the alkali metal lactate comprising powder.

11. The method of claim 1, wherein the aqueous concentrate is 80-100% (m/m)alkali metal lactate.

12. The method of claim 11, wherein the aqueous concentrate is 90-100% (m/m) alkali metal lactate.

\* \* \* \* \*

UNITED STATES PATENT AND TRADEMARK OFFICE
CERTIFICATE OF CORRECTION

PATENT NO. : 7,494,684 B2 Page 1 of 1
APPLICATION NO. : 10/265633
DATED : February 24, 2009
INVENTOR(S) : Eloy E. Urbano Cruz et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 5 days.

should read (*) Notice: Subject to any disclaimer, the term of this patent is extended or adjusted under 35 U.S.C. 154(b) by 255 days.

Signed and Sealed this

Twenty-second Day of June, 2010

David J. Kappos
*Director of the United States Patent and Trademark Office*